US005281618A

United States Patent [19]
Walter

[11] Patent Number: 5,281,618
[45] Date of Patent: Jan. 25, 1994

[54] STORAGE STABLE HIGH AZADIRACHTIN SOLUTION

[75] Inventor: James F. Walter, Ashton, Md.

[73] Assignee: W. R. Grace & Co.-Conn., New York, N.Y.

[21] Appl. No.: 948,195

[22] Filed: Sep. 21, 1992

[51] Int. Cl.$^5$ ..................... A01N 43/16; A01N 65/00
[52] U.S. Cl. .................. 514/453; 424/195.1
[58] Field of Search ............ 514/953; 424/195.1

[56] References Cited

U.S. PATENT DOCUMENTS

| | | | |
|---|---|---|---|
| 4,556,562 | 12/1985 | Larson | 424/195.1 |
| 4,946,681 | 8/1990 | Walter | 424/195.1 |
| 5,001,146 | 3/1991 | Carter et al. | 514/453 |
| 5,124,349 | 6/1992 | Carter et al. | 514/453 |

OTHER PUBLICATIONS

J. B. Stokes and R. E. Redfern; J. Environ. Sci. Health, A17(1), 57-65 (1982).
K. Feuerhake and H. Schmutterer; Journal of Plant Diseases and Protection, 89(12), 737-747 (1982).
D. R. Schroeder and K. Nakanishi; Journal of Natural Products, vol. 50, No. 2, 241-244, (Mar.-Apr. 1987).
J. D. Warthen, Jr. et al.; Journal of Liquid Chromatography, 7(3), 591-598 (1984).
Uebel et al., Journal of Liquid Chromatography, 2(6), 875-882 (1979).
K. Polasa and C. Rukmini; Fd. Chem. Toxic, vol. 25, No. 10, 763-766 (1987).
M. Muthusamy et al.; Neem Newsletter 5(4) Oct.-Dec., p. 48 (1988).
T. L. Ladd, Jr. et al.; J. Econ. Entomol. 77, 903-905 (1984).
J. D. Warthen, Jr.; Science and Education Administration, Agricultural Reviews and Manuals, Northeastern Series, No. 4, Apr. (1979).

*Primary Examiner*—John W. Rollins
*Attorney, Agent, or Firm*—Beverly K. Johnson

[57] ABSTRACT

Storage stable pesticide compositions comprising neem seed extracts which contain azadirachtin as the active pesticidal ingredient wherein the compositions are characterized by their non-degrading solvent systems and high concentrations, i.e., greater than 10 g/l, of azadirachtin. In one embodiment, the pesticide compositions contain solvent systems characterized as having greater than 50% by volume aprotic solvents and less than 15% by volume water. In a second embodiment, the pesticide compositions contain solvent systems characterized as having greater than 50% by volume alcohol and less than 5% by volume water.

27 Claims, No Drawings

STORAGE STABLE HIGH AZADIRACHTIN SOLUTION

BACKGROUND OF THE INVENTION

1. Field of the Invention

This invention relates to pesticide compositions, and more specifically to storage-stable pesticide formulations containing high concentrations, i.e., greater than 10 g/l, of azadirachtin as the active ingredient.

2. Description of the Prior Art

The biological activities of the neem tree seeds have long been recognized. Of primary importance are the potent pesticidal properties of azadirachtin, the main active ingredient in the neem seed. Azadirachtin is a tetranortriterpenoid that causes feeding inhibition and growth disruption in various insect, mite, nematode, etc. orders.

There are various methods known in the prior art to extract azadirachtin from neem seeds, including the use of solvents such as methanol, ethanol, water, methylene chloride, chloroform, hexane, methylethylketone, butanol, petroleum benzene, ether, acetone, methyl terbutyl ether, diethylcarbonate, etc. In general, it has been found that the efficiency of the extract yield can be increased by increasing the solvent polarity, i.e., from hexane to ethanol, ethanol to methanol, methanol to water, etc. However, while various studies have examined relative solvent extraction efficiencies, little attention has been focused on the shelf life stability of azadirachtin in solution.

The most significant limitation to the successful use of azadirachtin as a pesticide and insect repellant is the stability of the azadirachtin in solution. One study has shown that heat and sunlight (UV radiation) cause rapid degradation of azadirachtin. J. Environ. Sci. Health, A17(1), 57–65 (1982) by J. B. Stokes and R. E. Redfern. Sunlight degradation of azadirachtin can be effectively reduced by addition of Uv absorbing additives such as para-aminobenzoic acid (PABA), neem oil, angelica oil, castor oil, or calmus oil.

Some major factors known to affect the storage stability of azadirachtin are the concentration of azadirachtin in solution and the pH of the solution. U.S. Pat. No. 4,556,562 (Larson) discloses improvement in storage properties of azadirachtin in aqueous ethanol emulsions having no more than 10 g/l azadirachtin by adjusting the concentration of azadirachtin in the range 2000 to 4000 ppm and adjusting the pH in the range 3.5 to 6.0.

It has now been discovered that the concentration of azadirachtin in solution in a storage-stable composition can be increased in the presence of hydrophillic, aprotic solvents, in particular ketone and acetate solvents.

SUMMARY OF THE INVENTION

It is an object of this invention to provide an improved storage stable azadirachtin-containing neem pesticidal formulation having an increased concentration of azadirachtin.

Another object of this invention is to provide a process for preparing storage stable azadirachtin formulations wherein the formulation is characterized by a high concentration of azadirachtin in solution.

Another object of this invention is to provide a storage stable neem seed extract formulation having azadirachtin as the active pesticidal ingredient wherein the formulation is characterized by concentrations of greater than 10 g/l of azadirachtin in solution.

In accordance with the present invention, there have been provided certain novel non-degrading pesticide formulations containing azadirachtin as an active ingredient, said formulations characterized by greater concentrations of azadirachtin than available in prior known storage-stable azadirachtin containing compositions. As used herein, the term non-degrading relates to hydrophillic, aprotic solvents that do not cause the decomposition of azadirachtin in solution. The aprotic solvents of this invention are characterized by the absence of any acidic or basic functionalities. The azadirachtin formulations of this invention, by virtue of their increased concentrations of azadirachtin, offer reduced shipping costs and storage space and increased product safety and the ability to be used in ultra low volume spray equipment.

DETAILED DESCRIPTION

The present invention is directed to storage stable azadirachtin compositions which have been formulated using non-degrading solvent systems to have greater than 10 g/l of azadirachtin. As used herein, the term "storage stable" refers to formulations that have retained at least 80% of their active ingredient content after one year at room temperature (25° C.). The non-degrading solvent systems acceptable for use in the azadirachtin formulations of the invention, namely hydrophillic, "aprotic" solvents. In accordance with the present invention, azadirachtin formulations are provided with enhanced stability and high concentrations of azadirachtin.

Aprotic solvents are defined as polar solvents having moderately high dielectric constants, which do not contain acidic hydrogen, Morrison and Boyd, Organic Chemistry 3rd. Edition, 31 (1974). The various factors that determine whether a given solvent is protic or aprotic are only qualitatively understood. The proton donating or proton accepting interaction is usually greatest when the atom attached to the proton is nitrogen or oxygen. This behavior has been attributed to hydrogen bonding. In general, the hydrogen bond strength increases with increasing acidity of the proton-donating group, and increasing basicity of the proton-accepting group. Aprotic solvents suitable for use in this invention will be those solvents that do not contain acidic or basic functional groups and do not degrade into acids or bases, including, but not limited to, ketones, nitriles, substituted aromatics such as alkyl or halogenated aromatics, amides, sulfoxides, alkyl carbonates, chlorinated aliphatics, aromatic aldehydes, sulfones, ethers, esters, and the like, or mixtures thereof. The preferred aprotic solvents for use in this invention include, but are not limited to, acetone, 2-butanone, 3-methyl-2-butanone, cyclohexanone, acetonitrile, xylenes, chlorobenzene, methylene chloride, chloroform trichloroethane, ethylene chloride benzaldehyde, sulfolane, methyl-t-butyl ether, dibutyl ether, ethyl acetate, propyl acetate, amyl acetate, dimethylsulfoxide (DMSO), dimethylformamide (DMF), dimethylacetamide, diethylcarbonate, propylene carbonate, ethylene carbonate, and mixtures thereof. Various other solvents having the above aprotic characteristics are known to those skilled in the art, and the choice of a particular solvent is not per se critical to the invention, provided that azadirachtin has a high degree of solubility therein, and the solvent does not cause degradation of the azadirachtin by proton donating or proton accepting interactions.

The storage stable azadirachtin formulations of this invention can be prepared by either of two general procedures:

A first embodiment of this invention is to extract azadirachtin and neem oil together from dried neem seeds that have been coarsely ground to about 5 mesh. The ground neem seeds are extracted by using an aprotic solvent having azadirachtin solubility. This aprotic solvent extraction may be repeated to optimize the concentration azadirachtin in the solution.

Because dried neem seeds retain between 6 and 15% water, this polar solvent extraction, in addition to extracting azadirachtin, also extracts a significant amount of water. The neem seed extracts typically contain about 20% by volume water. Since water is an azadirachtin-degrading, protic solvent, its presence in neem seed extracts about the previously defined allowable limits will reduce the storage stability of the azadirachtin formulations. The allowable limit to the amount of water in a neem seed extract is dependent upon the aprotic/protic character of the particular solvent system of the extract. Specifically, if the solvent system is comprised of greater than 50% by volume aprotic solvents such as ketones or esters, the concentration of water must be less than 15% by volume of the total solution. Alternatively, if the solvent system comprises greater than 50% alcohol solvents, (which are more protic) the concentration of water must be less than 5%, preferably less than 2%, and most preferably less than 1% by volume of the total solution.

There are various techniques to reduce the concentration of water in the final solutions to within the above defined acceptable limits including, but not limited to, further extracting the neem seed extracts with a water-immiscible solvent, diluting the extracts with an appropriate aprotic solvent, or drying the extracts over a suitable adsorbent.

A preferred embodiment of this invention is to extract dried neem seeds that have been milled to a course powder of about 5 mesh with a non-polar, azadirachtin-insoluble insoluble aprotic solvent such as hexane to remove the neem oil from the seeds. This "cleanup" extraction is then followed by a second extraction of the defatted neem seeds using a more polar, azadirachtin-soluble solvent. As in the first embodiment, this extraction may be repeated to optimize the concentration of azadirachtin in the aprotic solvent extraction.

The hydrophillic, aprotic solvent extraction obtained from either embodiment is then cooled to a temperature of no greater than 10° C., preferably at a temperature of about 0° C. to 10° C., to precipitate residual waxes from the neem extract. The dewaxed extract is then treated to remove the solvent at a temperature and a pressure sufficient to obtain a concentration of azadirachtin of greater than 10 g/l azadirachtin to as high as the solubility of azadirachtin.

Azadirachtin pesticide formulations of the invention may be used alone or mixed with conventional inert agronomically or physiologically acceptable (i.e., plant and mammal compatible and/or pesticidally inert) diluents or extenders usable in conventional compositions or formulations as is well known in the art. If desired, adjuvants such as surfactants, sunscreens, stabilizers, antifoam agents and antidrift agents my also be added. Examples of compositions and formulations according to the invention include aqueous or other agronomically acceptable suspensions and dispersions, oily dispersions, pastes, dusting powders, wettable powders, emulsifiable concentrates, flowables, granules, baits, invert emulsions, aerosol compositions and fumigating candles.

In general, azadirachtin pesticide formulations of this invention preferably contain 5 to 50% emulsifying surfactant, 0 to 40% neem oil, 0 to 1% para-aminobenzoic acid or its esters, and less than 1% acetic acid or sodium hydroxide to adjust the PH to between about 3.8 and 4.2.

Azadirachtin pesticide compositions in accordance with the invention contain greater than 10 g/l azadirachtin in solution. Preferably, storage-stable compositions of the invention contain from about 11 g/l to about 200 g/l of azadirachtin or up to solubility of azadirachtin in solution.

Without further elaboration, it is believed that one skilled in the art, using the preceding detailed description can utilize the present invention to its fullest extent.

The following examples are provided to illustrate the invention in accordance with the principles of this invention, but are not to be construed as limiting the invention in any way except as indicated in the appended claims. All parts and percentages are by weight unless otherwise indicated.

EXAMPLE I

Three hundred (300) lbs. of neem seeds were ground to ~10 mesh and the shells were separated from the kernels by elutriation.

The kernels were then placed in an agitated tank and extracted with 2000 lbs. of hexane for three hours. The seeds were separated by centrifugation and the hexane evaporated to separate the extracted oil. The de-oiled kernels were then dried to remove the excess hexane and then extracted with ethylacetate to remove azadirachtin. The ethyl acetate neem extract contained 30 grams of azadirachtin per liter of ethylacetate. The ethylacetate was then evaporated at 55° C., 20 inches of Hg vacuum to concentrate the solution to 8% azadirachtin. The concentrate was then blended with 1% PABA, 20% Tween, and 32% propylacetate or 3% methylethylketone. The products were analyzed and found to contain less than 1% $H_2O$.

The stability of the solution was determined at 55° C. The results showed only a 10% decrease in azadirachtin titer on 21 days storage at 55° C.

We claim:

1. A storage-stable pesticide composition comprising a neem seed extract solution containing azadirachtin wherein the solution has at least 50% by volume aprotic solvent and less than 15% by volume water and wherein said solution is non-degrading to azadirachtin, has greater than 10 g/l of azadirachtin and is prepared from a dewaxed, azadirachtin-containing neem seed extract.

2. A storage-stable pesticide composition according to claim 1 wherein the neem seed extract solution contains from about 11 g/l to 200 g/l of azadirachtin in solution.

3. A storage-stable pesticide composition according to claim 1 wherein the aprotic solvent is selected from the group consisting of nitriles, substituted aromatics, chlorinated aliphatics, aromatic aldehydes, sulfones, ethers, esters, amides, sulfoxides, alkyl carbonates, ketones, and mixtures thereof.

4. A storage stable pesticide composition according to claim 1 wherein the solution further includes about 10 to 50 percent surfactant, 0 to 40% neem oil, 0 to 1 percent para-aminobenzoic acid or its esters, and the pH is adjusted to between 3.8 and 4.2 wherein the percentages are on a weight/weight basis.

5. A storage-stable pesticide composition comprising a neem seed extract solution containing azadirachtin wherein the solution has at least 50% by volume alcohol solvent and less than 5% by volume water and wherein said solution is non-degreading to azadirachtin, has greater than 10 g/l of azadirachtin and is prepared from a dewaxed, azadirachtin-containing neem seed extract.

6. A storage-stable pesticide composition according to claim 5 wherein the neem seed extract solution contains from about 11 g/l to solubility of azadirachtin.

7. A storage-stable pesticide composition according to claim 5 wherein the solution has at least 50% by volume alcohol solvent and less than 2% by volume water.

8. A storage-stable pesticide composition according to claim 5 wherein the solution has at least 50% by volume alcohol solvent and less than 1% by volume water.

9. A storage-stable pesticide composition according to claim 5 wherein the alcohol solvent is selected from the group consists of methanol, ethanol, propanol, isopropanol, butanol, 2-butanol, t-butanol, benzyl alcohol and mixtures thereof.

10. A storage-stable pesticide composition according to claim 5 wherein the solution is blended with about 10 to 50 percent surfactant, 0 to 40% neem oil, 0 to 1 percent para-aminobenzoic acid or its esters, and the pH is adjusted to between 3.8 and 4.2.

11. A process for the preparation of a storage-stable pesticide composition having greater than 10 g/l of azadirachtin comprising the steps of:
  a. extracting neem oil from coarsely ground neem seeds with a non-polar azadirachtin-insoluble aprotic solvent,
  b. extracting azadirachtin from the defatted neem seeds with a polar aprotic solvent, to obtain a neem solvent extract,
  c. cooling the neem solvent extract to a temperature sufficient to precipitate waxes from the extract;
  d. removing the polar aprotic solvent from the dewaxed neem solvent extract at a temperature and a pressure sufficient to obtain a neem extract having greater than 10 g/l of azadirachtin; and
  e. adjusting the azadirachtin extract from (d) by diluting with additional aprotic solvents or further extracting with a water-immiscible aprotic solvent to obtain a storage-stable pesticide composition having at least 50% by volume aprotic solvent and less than 15% by volume water.

12. A process according to claim 11 wherein the aprotic solvent is selected from the group consisting of ketones, nitriles, substituted aromatics, chlorinated aliphatics, aromatic aldehydes, sulfones, ethers, esters, amides, sulfoxides, alkyl carbonates, and mixtures thereof.

13. A process of claim 11 wherein the neem solvent extract is cooled to a temperature of no greater than 10° C. to dewax the extract in step (c).

14. A process of claim 13 wherein the neem solvent extract is cooled to a temperature of about 0° C. to 10° C. to dewax the extract in step (c).

15. A process of claim 11 wherein the solvent is removed from the dewaxed neem solvent extract by vacuum evaporation.

16. A process for the preparation of a storage-stable pesticide composition comprising the steps of:
  a. extracting neem oil from coarsely ground neem seeds with a non-polar azadirachtin insoluble aprotic solvent,
  b. extracting azadirachtin from the defatted neem seeds with an alcohol solvent to obtain a neem solvent extract;
  c. cooling the neem solvent extract at a temperature sufficient to precipitate waxes from the extract;
  d. removing the polar aprotic solvent from the dewaxed neem solvent extract at a temperature and a pressure sufficient to obtain a neem extract having greater than 10 g/l of azadirachtin; and
  e. adjusting the azadirachtin extract from (d) by either diluting or further extracting with a water-immiscible aprotic solvent to obtain a storage-stable pesticide composition having at least 50% by volume alcohol solvent and less than 5% by volume water.

17. A process according to claim 16 wherein the composition has at least 50% by volume alcohol solvent and less than 2% by volume water.

18. A process according to claim 16 wherein the composition has at least 50% by volume alcohol solvent and less than 1% by volume water.

19. A process according to claim 16 wherein the neem solvent extract is cooled to a temperature of about 0° to about 10° C. to dewax the extract in step (c).

20. A process according to claim 16 wherein the alcohol solvent is selected from the group consisting of methanol, ethanol, propanol, isopropanol, butanol, 2-butanol, t-butanol, benzyl alcohol, and mixtures thereof.

21. A process for the preparation of a storage-stable pesticide composition comprising the steps of:
  a. extracting azadirachtin and neem oil from coarsely ground neem seeds with a polar aprotic solvent;
  b. cooling the neem solvent extract at a temperature sufficient to precipitate waxes from the extract;
  c. removing the polar aprotic solvent from the dewaxed neem solvent extract at a temperature and a pressure sufficient to obtain a neem extract having greater than 10 g/l of azadirachtin; and
  d. adjusting the azadirachtin extract from (c) by either diluting or further extracting with a water-immiscible aprotic solvent to obtain a storage-stable pesticide composition having at least 50% by volume aprotic solvent and less than 15% by volume water.

22. A process according to claim 21 wherein the polar aprotic solvent is selected from the group consisting of ketones, nitriles, substituted aromatics, chlorinated aliphatics, aromatic aldehydes, sulfones, ethers, esters, amides, sulfoxides, alkyl carbonates, and mixtures thereof.

23. A process according to claim 21 wherein the neem solvent extract is cooled to a temperature of about 0° C. to about 10° C. to dewax the extract in step (c).

24. A process for the preparation of a storage-stable pesticide composition comprising the steps of:
  a. extracting azadirachtin and neem oil from coarsely ground neem seeds with and alcohol solvent;
  b. cooling the neem solvent extract at a temperature sufficient to precipitate wax from the extract;

c. removing the polar aprotic solvent from the dewaxed neem solvent extract at a temperature and a pressure sufficient to obtain a neem extract having greater than 10 g/l of azadirachtin; and e. adjusting the azadirachtin extract from (c) by either diluting or further extracting with a water-immiscible aprotic solvent to obtain a storage-stable pesticide composition having at least 50% by volume aprotic solvent and less than 5% by volume water.

25. A process according to claim 24 wherein the composition has at least 50% by volume alcohol solvent and less than 2% by volume water.

26. A process according to claim 25 wherein the composition has at least 50% by volume alcohol solvent and less than 1% by volume water.

27. A process according to claim 24 wherein the neem solvent extract is cooled to a temperature of about 0° C. to about 10° C. to dewax the extract in step (c).

* * * * *